US009210910B2

(12) United States Patent
van Zee (10) Patent No.: US 9,210,910 B2
(45) Date of Patent: Dec. 15, 2015

(54) LETTUCE VARIETY MULTIRED 54

(75) Inventor: Johan van Zee, Zaltbommel (NL)

(73) Assignee: Nunhems B.V., Nunhem (NL)

( * ) Notice: Subject to any disclaimer, the term of this patent is extended or adjusted under 35 U.S.C. 154(b) by 195 days.

(21) Appl. No.: 13/422,291

(22) Filed: Mar. 16, 2012

(65) Prior Publication Data

US 2012/0207911 A1 Aug. 16, 2012

(51) Int. Cl.
*A01H 1/00* (2006.01)
*A01H 4/00* (2006.01)
*A01H 5/00* (2006.01)
*A01H 5/10* (2006.01)
*A01H 5/12* (2006.01)
*C12N 5/04* (2006.01)

(52) U.S. Cl.
CPC .................................. *A01H 5/12* (2013.01)

(58) Field of Classification Search
None
See application file for complete search history.

(56) References Cited

U.S. PATENT DOCUMENTS

| | | | |
|---|---|---|---|
| 5,349,124 | A | 9/1994 | Fischhoff |
| 6,118,055 | A | 9/2000 | Livesey |
| 2008/0222949 | A1 | 9/2008 | Bissonnette |
| 2009/0106867 | A1 | 4/2009 | Moor |
| 2009/0271897 | A1 | 10/2009 | Gibson |
| 2012/0144517 | A1* | 6/2012 | Zee .............................. 800/265 |

FOREIGN PATENT DOCUMENTS

EP 1197137 11/2004

OTHER PUBLICATIONS

Whei-Lan Teng et al., Rapid Regeneration of Lettuce from Suspension, Culture HortScience (1992) 27(9), pp. 1030-1032.
Whei-Lan Teng et al., Regenerating Lettuce from Suspension Culture in a 2-Liter BioreactorHortScience (1993) 28(6), pp. 669-671.
Peter Halmer, Commercial seed treatment technology in "Seed technology and its biological basis", Michael Black Eds. (2000), pp. 257-286.
H.J. Hill et al., Primed Lettuce Seeds Exhibit Increased Sensitivity to Moisture Content During Controlled Deterioration, HortScience (2007) 42(6), pp. 1436-1439.
Takeru Gonai et al., Abscisic acid in the thermoinhibition of lettuce seed germination and enhancement of its catabolism by gibberellin, Journal of Experimental Botany (2004) vol. 55, No. 394, pp. 111-118.
Louise Jackson et al., Iceberg Lettuce Production in California, Publication 7215, ISBN 978-1-60107-007-4, 1996.
Ritsuko Murakami et al., Histological Observations on the Formulation of Meristematic Colonies Derived from Lettuce (*Lactuca sativa* L.) Protoplasts, Plant Tissue Culture Letters (1996) 13(3), pp. 339-341.
Allard, John Wiley & Sons, Inc.: Principles of plant breeding, Library of Congress Catalog Card No. 60-14240 (1960), pp. 119-128.
M. Hayashi et al., Development of SCAR and CAPS markers linked to a recessive male sterility gene in lettuce (*Lactuca sativa* L.), Euphytica (2011) vol. 180(3), pp. 429-436.
Arlette Reynaerts et al., Engineered genes for fertility control and their application in hybrid seed production, Scientia Horticulturae (1993) 55 (1-2), pp. 125-139.
Ian S. Curtis et al., Genomic male sterility in lettuce, a baseline for the production of F, hybrids, Plant Science Limerick (1996) 113(1), pp. 113-119.
Peter Vos et al., AFLP: a new technique for DNA fingerprinting 1995, Nucleic Acids Research (1995) vol. 23, No. 21, pp. 4407-4414.
F.A. Van Eeuwijk et al., Statistical aspects of essential derivation, with illustrations based on lettuce and barley, Euphytica (2004) vol. 137, pp. 129-137.
B.R. Glick and J.E. Thompson Eds., Procedures for Introducing Foreign DNA into Plants, CRC Press, Inc., Boca Raton (1993), pp. 67-88.
C.L. Armstrong, "The First Decade of Maize Transformation: A Review and Future Perspective" Maydica (44) (1999), pp. 101-109.
B.R. Glick and J.E. Thompson Eds., Vectors for Plant Transformation, CRC Press, Inc., Boca Raton (1993), pp. 89-119.
Robert T. Fraley, Expression of bacterial genes in plant cells, Proc. Natl. Acad. Sci. USA (1983) vol. 80, pp. 4803-4807.
Peter J. M. Van Den Elzen et al., Plant Molecular Biology (1985) vol. 5, pp. 299-302.
Martin Chalfie et al., Green Fluorescent Protein as a Marker for Gene Expression, Science (1994) 263, pp. 802-805.
Thomas W. Becker et al., The cab-m7 gene: a light-inducible, mesophyll-specific gene of maize, Plant Molecular Biology (1992) 20, pp. 49-60.
Cheryl A.P. Knox et al., Structure and organization of two divergent α-amylase genes from barley, Plant Mol. Biol. (1987) 9, pp. 3-17.
Marie-Christine Chupeau et al., Transgenic Plants of Lettuce (*Lactuca sativa*) obtained through Electroporation of Protoplasts, Bio/Technology 7 (1989), pp. 503-508.
James A. Elliot et al., Collapse of Single-Wall Carbon Nanotubes is Diameter Dependent, Physical Review Letters (2004) vol. 92, pp. 095501-095504.
Gunther Neuhaus and Germàn Spangenberg, Plant transformation by microinjection techniques, Physiologia Plantarum (1990) 79 (1), pp. 213-217.
Louise Jackson et al., Leaf Lettuce Production in California, Publication 7216 ISBN 978-1-60107-008-1, 1996.
Xinrun Zhang et al., Genotypic effects on tissue culture response of lettuce cotyledons, J. Genet. & Breed. (1992) 46, pp. 287-290.

* cited by examiner

*Primary Examiner* — Eileen B O Hara (57) ABSTRACT

The present invention relates to plants of a lettuce variety NUN 09054 LT (referred to as "MULTIRED 54") and, seeds and progeny thereof. The invention further relates to methods for producing a lettuce plant by traditional breeding methods. Moreover, the invention relates to a method for producing a lettuce plant containing in its genetic material one or more transgenes.

21 Claims, 1 Drawing Sheet

LETTUCE VARIETY MULTIRED 54

This application claims priority under 35 U.S.C. 119(a)-(d) to CPVO Application No. 2011/2208, filed by Nunhems B.V. on 14 Sep. 2011, the disclosure of which is herein incorporated by reference in its entirety.

FIELD OF THE INVENTION

The present invention relates to the field of plant breeding. In particular, the invention provides for a new and distinct variety of lettuce designated NUN 09054 LT (or "NUN 09054" or "09054" or "MULTIRED 54").

All cultivated forms of lettuce belong to the highly polymorphic species *Lactuca sativa* that is grown for its edible head and leaves. *Lactuca sativa* is in the Cichoreae tribe of the Asteraceae (Compositae) family. Lettuce is related to chicory, sunflower, aster, dandelion, artichoke and chrysanthemum. *L. sativa* is one of about 300 species in the genus *Lactuca*.

Fresh lettuce is available in the United States year-round although the greatest supply is from May through October. For planting purposes, the lettuce season is typically divided into three categories, early, mid and late, with the coastal areas planting from January to August, and the desert regions planting from August to December. Fresh lettuce is consumed nearly exclusively as fresh, raw product and occasionally as a cooked vegetable.

The development of commercial lettuce cultivars requires the development of lettuce varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Lifestyles change and the demand from restaurants and catering firms for colorful and interesting garnish for sandwiches and ready-to-use processed salads continue to rise. As a result, there is a demand for breeding companies to develop new varieties with specific shapes of leaves, specific average size of leaves, prominent color and a wide variety of texture, as well as good yield.

SUMMARY OF THE INVENTION

The invention provides for a new Cutting/Leaf lettuce variety designated NUN 09054, representative seed of said variety having been deposited under Accession Number NCIMB 42205, and plant parts of the new variety such as (harvested) leaves, or parts of the leaves. Non-limiting examples for parts of said plant are microspore, pollen, ovary, ovule, flower, stalk, leaf, head, shoot, shoot tip, seed, embryo, embryo sac, cutting, root, root tip, pistil, anther, cotyledon, hypocotyl, meristematic cell, stem, cell, in vitro cell cultures or tissue cultures, protoplast, meristem, fruit, petiole, bud or parts of any of these such as parts of leaves. In some embodiments, parts of a lettuce plant designated NUN 09054 are provided which are suitable for sexual reproduction or vegetative reproduction, or a tissue culture or cell culture of a lettuce plant designated NUN 09054 is provided.

The invention also provides for seeds of the new variety, representative seed of said variety having been deposited under Accession Number NCIMB 42205, a plant, or a part thereof (such as a lettuce head or leaves), produced by growing said seed.

In a further aspect, the invention provides a plant which is regenerated from a part of the lettuce plant designated NUN 09054 that is suitable for vegetative reproduction or a plant which is regenerated from a cell or tissue culture of a plant designated NUN 09054.

Also provided are one or more progeny plants (offspring or descendants) of a lettuce plant designated NUN 09054 obtained by further breeding with said variety designated NUN 09054. Said progeny plant(s) has/have essentially all physiological and morphological characteristics of variety NUN 09054 when grown under the same environmental conditions. In one embodiment, said progeny plant(s) has/have a brown (to black) seed color (see USDA criteria); a moderately dentated apical margin of fourth leaf (see USDA criteria); a moderately dentated basal margin of fourth leaf (see USDA criteria); a medium undulation of fourth leaf (see USDA criteria); the undulation of the apical margin of mature leaves (at harvest mature outer leaves) is strong.

Moreover, also an Essentially Derived Variety (EDV) of a lettuce plant designated NUN 09054 is provided, e.g., an Essentially Derived Variety of NUN 09054 having one or two physiological and/or morphological characteristics which are different from those of NUN 09054 and which otherwise has essentially all physiological and morphological characteristics when grown under the same environmental conditions of a lettuce plant designated NUN 09054 obtainable by selecting a natural or induced mutant, or a somaclonal variant from a population of plants designated NUN 09054.

In another aspect the invention refers to packages, e.g., a container, a bag and the like, comprising at least one of the following: seeds or seed pellets of lettuce variety designated NUN 09054, lettuce plant(s) designated NUN 09054, parts thereof (e.g. heads or loose leaves), progeny of a lettuce plant designated NUN 09054, parts thereof, EDV of a plant designated NUN 09054 or parts thereof.

Also provided is a food or feed product comprising at least a part of a lettuce plant designated NUN 09054, progeny thereof or a EDV thereof.

In further aspects, the invention provides methods of producing a lettuce plant, comprising crossing a lettuce plant designated NUN 09054 with a second lettuce plant one or more times and/or selfing the lettuce plant designated NUN 09054 one or more times, and selecting progeny from said crossing and/or selfing.

Also provided is a method of producing a lettuce plant derived from NUN 09054 comprising the steps of:

(a) preparing a progeny plant derived from NUN 09054 by crossing the plant designated NUN 09054 with itself or with a second lettuce plant;

(b) crossing the progeny plant with itself or a second lettuce plant to produce a seed of a progeny plant of a subsequent generation;

(c) growing a progeny plant of a subsequent generation from said seed and crossing the progeny plant of a subsequent generation with itself or a second lettuce plant; and (d) repeating step b) and/or c) for at least 1 more generation to produce a lettuce plant derived from NUN 09054.

In another aspect the invention provides a method of producing a hybrid lettuce seed comprising crossing a first parent lettuce plant with a second parent lettuce plant and harvesting the resultant hybrid lettuce seed, wherein said first parent lettuce plant or said second parent lettuce plant is a lettuce plant designated NUN 09054.

Also provided is hybrid lettuce seed (from which a hybrid plant can be grown) produced from crossing a first parent lettuce plant with a second parent lettuce plant and harvesting the resultant hybrid lettuce seed, wherein said first parent lettuce plant or said second parent lettuce plant is a plant designated NUN 09054. Moreover, also provided are hybrid lettuce plants which are grown from a hybrid lettuce seed whereof one parent is a plant designated NUN 09054.

In another aspect the invention provides a method of introducing a single locus conversion into a plant designated NUN 09054, representative seed of which having been deposited under Accession Number NCIMB 42205, comprising
  (a) crossing a plant designated NUN 09054 with a second plant comprising a desired single locus to produce an $F_1$ progeny plant;
  (b) optionally selfing said $F_1$ progeny plant to produce an $F_2$ progeny plant having said single locus;
  (c) optionally crossing said $F_1$ or $F_2$ progeny plant of step (a) or step (b), respectively, with a plant of NUN 09054, representative seed of which having been deposited under Accession Number NCIMB 42205, to produce backcross progeny plants;
  (d) optionally selecting backcross progeny plants that have the single locus and otherwise essentially all physiological and morphological characteristics when grown under the same environmental conditions of a plant designated NUN 09054; and
  (e) optionally repeating steps (c) and (d) one or more times in succession to produce selected second or higher backcross progeny plants that comprise the single locus and otherwise comprise essentially all physiological and morphological characteristics when grown under the same environmental conditions of a plant designated NUN 09054.

In one embodiment, said single locus confers a trait, wherein the trait is pest resistance or disease resistance such as resistance against *Nasonovia ribisnigri* NR:0 or resistance against *Nasonovia ribisnigri* NR:1. Further pest or disease resistances are, e.g., resistance against downy mildew, e.g., at least one race selected from the group consisting of races Bl:1 to 28 and other known *Bremia lactucae* races, *Sclerotinia* rot, *Botrytis*, powdery mildew, anthracnose, bottom rot, corky root rot, lettuce mosaic virus, big vein, lettuce aphid, beet western yellows and aster yellows, *Sclerotinia minor* (leaf drop), *Sclerotinia sclerotiorum* (leaf drop), *Rhizoctonia solani* (bottom drop), *Erysiphe cichoracearum* (powdery mildew), *Fusarium oxysporum* f. sp. *lactucae* (*Fusarium* wilt), lettuce infectious yellows virus (LIYV), lettuce mosaic virus (LMV), Cucumber mosaic virus (CMV), Beet western yellows virus (BWYV), and Alfalfa mosaic virus (AMV).

In another embodiment the trait conferred by said single locus is another trait, such as a morphological or physiological trait, herbicide resistance, stress tolerance or stress resistance (e.g. drought tolerance), enhanced yield, etc.

A further aspect of the invention relates to a method of producing transgenic progeny of a plant designated NUN 09054 wherein said progeny has at least the essential physiological and morphological characteristics when grown under the same environmental conditions of the variety designated NUN 09054 and further comprises a desired trait, said method comprising transforming a NUN 09054 plant with at least one transgene that confers said desired trait or crossing a plant designated NUN 09054 with a lettuce plant comprising said desired trait so that the genetic material of the progeny that results from the cross contains the transgene(s). Moreover, also transgenic plants produced by this method are provided herewith.

PICTURE

DETAILED DESCRIPTION

All patent and non-patent literatures cited herein are incorporated by reference in their entireties.

"Lettuce" refers herein to plants of the species *Lactuca sativa* L.

The terms "NUN 09054 LT", "lettuce plant designated NUN 09054", "NUN 09054", "MULTIRED 54" or "variety designated NUN 09054" refer to a lettuce plant/ variety of lettuce, representative seed of which having been deposited under Accession Number NCIMB 42205.

"USDA descriptors" are the plant variety descriptors described for lettuce in the "Objective description of Variety Lettuce (*Lactuca sativa* L.)", ST-470-1 (dated Jul. 1, 2009) as published by U.S. Department of Agriculture, Agricultural Marketing Service, Science and Technology, Plant Variety Protection Office, Beltsville, Md. 20705 (available on the world wide web at www.ams.usda.gov/AMSv1.0/) and which can be downloaded from the world wide web at www.ams.usda.gov/AMSv1.0/getfile?dDocName=stelprdc5069208.

"UPOV descriptors" are the plant variety descriptors described for lettuce in the "Guidelines for the Conduct of Tests for Distinctness, Uniformity and Stability," TG/013/10 (Geneva 2006), as published by UPOV (International Union for the Protection of New Varieties and Plants, available on the world wide web at upov.int) upov.int/en/publications/tg_rom/tg_index.html. Likewise, "UPOV methods" to determine specific parameters for the characterization of lettuce are described at upov.int.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

As used herein, the term "plant" includes the whole plant or any parts such as plant organs (e.g., harvested or non-harvested leaves, etc.), plant cells, plant protoplasts, plant cell or tissue cultures from which whole plants can be regenerated, plant callus, plant cell clumps, plant transplants, seedlings, plant cells that are intact in plants, plant clones or micro propagations, or parts of plants (e.g., harvested tissues or organs), such as plant cuttings, vegetative propagations, embryos, pollen, ovules, flowers, leaves, heads, seeds, clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves.

"Cotyledon" refers to one of the first leaves of the embryo of a seed plant; typically one or more in monocotyledons, two in dicotyledons and two or more in gymnosperms.

"Tissue Culture" refers to a composition comprising isolated cells of the same or a different type or a collection of such cells organized into parts of a plant. Tissue culture of various tissues of lettuce and regeneration of plants therefrom is well known and widely published (see, e.g., Teng et al., HortScience. 1992, 27 (9): 1030-1032 Teng et al., HortScience. 1993, 28 (6): 669-1671, Zhang et al., Journal of Genetics and Breeding. 1992, 46 (3): 287-290).

"Harvested plant material" refers herein to plant parts (e.g., leaves detached from the whole plant) which have been collected for further storage and/or further use.

"Harvested seeds" refers to seeds harvested from a line or variety, e.g., produced after self-fertilization or cross-fertilization and collected.

"Head" as used herein refers to lettuce heads, i.e., the plant without the root system, for example substantially all harvested leaves (although this variety is a "loose-leaf" type). Encompassed are immature leaves (e.g. "baby leaf") and mature leaves.

The "base" of a plant is the part of a lettuce plant where the leaves are attached to the root system of the plant.

"Core length" of the internal lettuce stem is measured from the base of the cut and trimmed head to the tip of the stem.

"Head weight" refers to the mean weight of saleable lettuce head, cut and trimmed to market specifications.

"Head diameter" refers to the mean diameter of the cut and trimmed head, sliced vertically, and measured at the widest point perpendicular to the stem.

"Head height" refers to the mean height of the cut and trimmed head, sliced vertically, and measured from the base of the cut stem to the leaf tip.

"Core Length to Head Diameter Ratio (CLHD Ratio)" refers to the mean core length/head diameter ratio. It is calculated by dividing the mean core length with the mean head diameter. This is an indication of the head shape and of the ability of a lettuce plant to reduce the amount of surface which is on or close to the ground.

"Ground" refers to the surrounding of the aerial tissues of a lettuce plant in which it is grown, or which is placed on the growing medium (e.g. a foil covering the growing medium such as soil but which does not cover the aerial plant, e.g., there is a hole in the foil through which the lettuce plant is growing).

A plant having "essentially all the physiological and morphological characteristics" means a plant having the physiological and morphological characteristics when grown under the same environmental conditions of the plant from which it was derived, e.g. the progenitor plant, the parent, the recurrent parent, the plant used for tissue- or cell culture, etc., except for the characteristic(s) derived from a converted or introduced gene or trait.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Progeny" as used herein refers to plants derived from a plant designated NUN 09054. Progeny may be derived by regeneration of cell culture or tissue culture or parts of a plant designated NUN 09054 or selfing of a plant designated NUN 09054 or by producing seeds of a plant designated NUN 09054. In further embodiments, progeny may also encompass plants derived from crossing of at least one plant designated NUN 09054 with another lettuce plant of the same or another variety or (breeding) line, or wild *Lactuca* plants, backcrossing, inserting of a locus into a plant or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

An "Essentially Derived Variety" (EDV) shall be deemed to be essentially derived from another variety, "the initial variety", under the following circumstances: (i) it is predominantly derived from the initial variety, or from a variety that is itself predominantly derived from the initial variety, while retaining the expression of essentially all characteristics that result from the genotype or combination of genotypes of the initial variety; and (ii) it is clearly distinguishable from the initial variety (e.g., one, one or more, two, two or more, three, three or more characteristics are different from the initial variety); and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, the selection of a variant individual from plants of the initial variety, backcrossing, or transformation by genetic engineering. Such a variant may be selected at any time, e.g. in the field or greenhouse, during breeding, during or after in vitro culture of cells or tissues, during regeneration of plants, etc.

"Plant line" is for example a breeding line which can be used to develop one or more varieties.

"Hybrid" refers to the seeds harvested from crossing one plant line or variety with another plant line or variety.

"$F_1$ hybrid" refers to the first generation progeny of the cross of two nonisogenic plants.

"Crossing" refers to the mating of two parent plants. Equally "Cross-pollination" refers to fertilization by the union of two gametes from different plants.

"Backcrossing" refers to a process in which a breeder repeatedly crosses hybrid progeny, for example a first generation hybrid ($F_1$), back to one of the parents of the hybrid progeny. Backcrossing can be used to introduce one or more single locus conversions from one genetic background into another. The terms "gene converted" or "conversion plant" in this context refer to plants which are developed by backcrossing wherein essentially all of the desired morphological and physiological characteristics of an inbred are recovered in addition to the one or more genes transferred into the inbred via the backcrossing technique or via genetic engineering.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, fruit, and petiole. When a whole plant is regenerated by vegetative propagation, it is also referred to as a vegetative propagation.

"Selfing" refers to self-pollination of a plant, i.e., the transfer of pollen from the anther to the stigma of the same plant.

"Single Locus Converted (Conversion) Plant" refers to plants which are developed by plant breeding techniques comprising or consisting of backcrossing, wherein essentially all of the desired morphological and physiological characteristics of a lettuce variety are recovered in addition to the characteristics of the single locus having been transferred into the variety via the backcrossing technique and/or by genetic transformation.

"Transgene" or "chimeric gene" refers to a genetic locus comprising a DNA sequence which has been introduced into the genome of a lettuce plant by transformation. A plant comprising a transgene stably integrated into its genome is referred to as "transgenic plant".

"Substantially equivalent" refers to a characteristic that, when compared, does not show a statistically significant difference (e.g., p=0.05) from the mean.

"Average" refers herein to the arithmetic mean.

"First water date" refers to the date the seed first receives adequate moisture to germinate. This can and often does equal the planting date.

"Maturity date" refers to the stage when the plants are of full size or optimum weight, in marketable form or shape to be of commercial or economic value. This is also the time point when measuring parameters of "mature" leaves.

The term "mean" refers to the arithmetic mean of several measurements. The skilled person understands that the appearance of a plant depends to some extent on the growing conditions of said plant. Thus, the skilled person will know typical growing conditions for lettuce of the types described herein. The mean, if not indicated otherwise within this application, refers to the arithmetic mean of measurements on at least 10 different, randomly selected plants of a variety at a required developing stage (e.g., fourth leaf or mature).

The present invention provides a new type of lettuce (*Lactuca sativa*) variety, designated NUN 09054. Lettuce variety designated NUN 09054 is of the Cutting/Leaf Type (USDA criteria). The objective of the cross was to develop a Cutting/Leaf variety with a prominent shape of its red mature leaves.

Variety NUN 09054 is most similar to the commercially available variety OBREGON. However, NUN 09054 differs from OBREGON in one or more, e.g., at least two, at least three, optionally all morphological and/or physiological characteristics listed in the following (see also Table 1), when grown under the same environmental conditions:
- the color of seeds of NUN 09054 is black (grey brown) (see USDA criteria) whereas the color of OBREGON is white (silver gray) (see USDA criteria);
- the basal margin of fourth leaf of NUN 09054 is incised compared to the basal margin of fourth leaf of OBREGON which is coarsely dentate (see USDA criteria);
- anthocyanin is distributed throughout fourth leaf of NUN 09054 whereas anthocyanin is only present in the margin of fourth leaf of OBREGON (see USDA criteria);
- anthocyanin concentration in fourth leaf of NUN 09054 is intense whereas the anthocyanin concentration in fourth leaf of OBREGON is moderate (see USDA criteria);
- the incision depth of mature leaves of NUN 09054 is deep (such as in Great Lakes 659) whereas the incision depth of mature leaves of OBREGON is moderate (such as in Vanguard) (see USDA criteria);
- the green color of mature leaves of NUN 09054 is dark green whereas the green color of mature leaves of OBREGON is light green (e.g VHS color chart 144A vs 144C) (see USDA criteria);
- the distribution of anthocyanin is throughout the mature leaves of NUN 09054 whereas anthocyanin is only present in the margin of fourth leaf of OBREGON (see USDA criteria);
- anthocyanin concentration in mature leaf of NUN 09054 is intense whereas the anthocyanin concentration in mature leaf of OBREGON is moderate (see USDA criteria);
- mature leaves of NUN 09054 are glossy whereas mature leaves of OBREGON are dull (see USDA criteria).

The morphological and/or physiological differences between NUN 09054 and other known varieties, such as OBREGON or GRAND RAPIDS (which is a standard regional check variety) can easily be established by growing NUN 09054 next to the other varieties (in the same field or greenhouse under the same environmental conditions), preferably in several locations which are suitable for lettuce cultivation, and measuring morphological and/or physiological characteristics of a number of plants (e.g., to calculate an average value (of at least 10 or even more plants which were grown under the same conditions) and to determine the variation range/uniformity within the variety). Differences between varieties can be determined throughout the growing period as long as the plants to be compared developed the parts of said plants which are compared with each other. For example, mature leaves can be compared with each other when the plants developed these leaf stages. This can be the case, e.g., after 20, after 25, after 30 days or at harvest day. Comparative varieties which can be grown in the same field are GRAND RAPIDS, OBREGON and others. These are commercially available varieties.

For example, trials can be carried out in Spain, the Netherlands or the USA whereby e.g., seed characteristics, cotyledon characteristics, fourth leaf characteristics, mature plant characteristics, such as plant head diameter, head shape, head size, head weight, butt and core characteristics, time of bolting (number of days from first water date to seed stalk emergence), seed stalk characteristics, bolter habit, maturity (earliness of harvest-mature head formation), regional and/or seasonal adaptation, pest and/or disease resistance/susceptibility can be measured and directly compared. Also resistance against physiological stresses, such as tip burn, heat-, drought-, cold-resistance, etc. and/or post-harvest characteristics of heads or leaves can be compared, such as pink rib, russet spotting, rusty brown discoloration, internal rib necrosis (blackheart, grey rib, grey steak) and brown stain can be measured using known methods, e.g. as indicated in the USDA descriptors. The morphological and/or physiological characteristics may vary with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the RHS-Chart (see, e.g., world wide net: http://www.rhs.org.uk/Plants/RHS-Publications/RHS-colour-charts).

Seeds

The present invention does not only provide plants designated NUN 09054. Also provided are seeds of lettuce variety NUN 09054. A representative sample of said seeds (at least 2500 seeds) has been deposited under the Budapest Treaty with Accession Number NCIMB 42205.

Seeds of NUN 09054 are obtainable by, e.g., growing plants from the seeds deposited under Accession number NCIMB 42205 and allowing, e.g., self-pollination and/or cross-pollination and collecting seeds from the resulting plants. The resultant NUN 09054 seeds can be grown to produce plants designated NUN 09054. Moreover, a seed dedicated NUN 09054 also refers to a seed wherein the plant grown therefrom shows essentially all characteristics of NUN 09054. Seeds of NUN 09054 are also obtainable by vegetative propagation from plant cells or tissue of a plant grown from seeds of NUN 09054.

In one embodiment, a plurality of NUN 09054 seeds are packaged into small and/or large containers (e.g., bags, cartons, cans, etc.). The seeds may be pelleted prior to packing (to form pills or pellets) and/or treated with various compounds, such as seed coatings.

Seed pelleting can be combined with film coating (Halmer, P. 2000. Commercial seed treatment technology. In: Seed technology and its biological basis. Eds: Black, M. and Bewley, J. D., pages 257-286). Pelleting creates round or rounded shapes, which are easily sown with modern sowing machines. A pelleting mixture typically contains seeds and at least glue and filler material. The latter could be, for example, clay, mica, chalk or cellulose. In addition, certain additives can be included to improve particular properties of the pellet, e.g., a seed treatment formulation comprising at least one insecticidal, acaricidal, nematicidal or fungicidal compound can be added directly into the pelleting mixture or in separate layers. A seed treatment formulation can include one of these types of compounds only, a mixture of two or more of the same type of compounds or a mixture of one or more of the same type of compounds with at least one other insecticide, acaricide, nematicide or fungicide.

Formulations especially suitable for the application as a seed treatment can be added to the seed in the form of a film coating including also the possibility of using the coating in or on a pellet, as well as including the seed treatment formulation directly into the pellet mixture. Characteristically, a film coating is a uniform, dust-free, water permeable film, evenly covering the surface of all individual seeds (Halmer, P. 2000. Commercial seed treatment technology. In: Seed technology and its biological basis. Eds: Black, M. and Bewley, J. D., pages 257-286). Besides the formulation, the coating mixture generally also contains other ingredients such as water, glue (typically a polymer), filler materials, pigments and certain additives to improve particular properties of the coating. Several coatings can be combined on a single seed.

In addition, several combinations with film coating are possible: the film coating can be added on the outside of the pellet, in between two layers of pelleting material, and directly on the seed before the pelleting material is added. Also more than 1 film coating layer can be incorporated in a single pellet. A special type of pelleting is encrusting. This technique uses less filler material, and the result is a 'mini-pellet'.

Seeds may also be primed. Of all the commercially planted vegetable seeds, lettuce is the most often primed.

Priming is a water-based process that is performed on seeds to increase uniformity of germination and emergence from the soil, and thus enhance vegetable stand establishment. Priming decreases the time span between the emergence of the first and the last seedlings. Methods how to prime lettuce seeds are well known in the art (see, e.g., Hill et al HortScience 42 (6): 1436, 2007).

Plant and Parts Thereof.

Also provided are parts of the lettuce plants designated NUN 09054 such as microspores, pollen, ovaries, flowers, stalks, heads, ovules, leaves, shoots, seeds, embryos, embryo sacs, roots, cuttings, stems, cells, protoplasts, meristems, buds etc. of variety NUN 09054, or parts of any of these. Such parts may be (part of) sexual reproduction tissues, which include, without limitation microspores, pollen, flowers, ovaries, ovules, embryo sacs and egg cells, or vegetative cells or tissues, which include, without limitation cuttings, roots, stems, cells or protoplasts, leaves, cotyledons, meristems and buds.

Moreover, there is provided a cell culture or tissue culture of lettuce variety NUN 09054 in which the cell- or tissue culture is derived from a tissue such as, for example and without limitation, leaves, pollen, embryos, cotyledon, hypocotyls, meristematic cells, roots, root tips, anthers, flowers, seeds or stems. For example, leaf-, hypocotyl- or stem-cuttings may be used in tissue culture.

Also provided are lettuce plants regenerated from the above-described plant parts, or regenerated from the above-described cell or tissue cultures, said regenerated plant having essentially all the morphological and physiological characteristics of lettuce variety NUN 09054. These plants can also be referred to as "vegetative propagations of NUN 09054".

Also provided are harvested leaves and/or heads of NUN 09054 and packages comprising a plurality of leaves and/or heads of NUN 09054 such as 1, 2, 3, 4, 5, 12, 12, 20 heads.

Growing Plants

Lettuce plants can be produced by seeding directly in the ground (e.g., soil such as soil in a field) or by germinating the seeds in controlled environment conditions (e.g., greenhouses) and then transplanting the seedlings into the field (see, e.g., Gonai et al., J. of Exp. Bot., 55 (394): 111, 2004; Louise Jackson et al, Publication 7215 ISBN 978-1-60107-007-4 and Publication 7216 ISBN 978-1-60107-008-1 and the world wide web at "anrcatalog.ucdavis.edu" search: lettuce for cultivation, harvesting, handling and postharvest methods commonly used). Lettuce may also be grown in tunnels.

Moreover, lettuce can be grown in hydroponic cultures as described in, e.g., US 2008/0222949.

Hydroponics is the cultivation of plants without soil. There are 6 basic types of hydroponic systems: Wick, Raft (also called Water Culture), Ebb and Flow (also called Flood & Drain), Drip, Nutrient Film Technique, and Aeroponic. There are hundreds of variations on these basic types of systems, and most hydroponics systems can be described as a variation or combination of these six types.

In wick systems, plants are grown in a soil-less growing medium and a solution containing water and nutrients is delivered using wicks that absorb the solution from a reservoir and deliver the solution to the growing medium. The roots of the plants are optionally prevented from or allowed to grow in the solution.

In raft systems, plants are grown in a soil-less growth medium that is floated by a raft on the surface of a solution containing water and nutrients. The roots of the plants are optionally prevented from or allowed to grow in the solution.

In Ebb and Flow systems, plants are grown in a soil-less growth medium in a flooding tray. Solution containing water and nutrients is intermittently delivered to the flooding tray and then returned to a reservoir. The plant roots are directly or indirectly contacted by the solution in the flooding tray. Optionally the solution is delivered by a pump and returned by gravity.

In drip systems, plants are grown in a soil-less growing medium. A solution containing water and nutrients is delivered in drips to the growing medium. The solution that is not used by the plants is either recycled (recovery systems) or discarded (non-recovery systems). In recovery systems, although there often is a reservoir, the plant roots are typically prevented from growing directly in the solution.

Nutrient film technique (N.F.T.) systems constantly deliver a thin film of a nutrient and water containing solution. The plants are grown in a soil-less growth medium and the roots are allowed to grow outside the medium into the surrounding air or the plants are grown directly suspended in the air without a growing medium. The roots that grow in the air are constantly contacted by the thin film of solution. Typically the solution is recycled. Optionally the solution is delivered by a pump and returned by gravity.

Aeroponic systems deliver the solution as a fine spray. The plants are grown in a soil-less growth medium and the roots are allowed to grow outside the medium into the surrounding air or the plants are grown directly suspended in the air without a growing medium. The roots that grow in the air are intermittently sprayed or misted with a solution containing water and nutrients. The roots of the plants are optionally prevented from or allowed to grow in the solution.

Furthermore, different lettuce varieties may be grown as "composite lettuce" (see, e.g., EP 1 197 137 A1).

Plants and Progeny

In another embodiment, plants and parts of lettuce variety designated NUN 09054 and progeny of lettuce variety designated NUN 09054 are provided, e.g., grown from seeds, produced by sexual or vegetative reproduction, regenerated from the above-described plant parts, or regenerated from cell or tissue culture of the lettuce variety designated NUN 09054, in which the reproduced (seed propagated or vegetatively propagated) plant has all or essentially all morphological and physiological characteristics of lettuce variety designated NUN 09054, e.g., as outlined in table 1. In one embodiment, said progeny of the lettuce variety designated NUN 09054 can be modified in one, two, three, four or five characteristics (e.g. different shape of apical margin of leaves or further resistances), in which the modification is a result of, for example and without limitation, mutagenesis or transformation with a transgene. A progeny can be a first generation progeny or a progeny up to generation two, three, four, five, six, seven or even higher.

Furthermore, the invention provides for progeny of variety NUN 09054 such as progeny obtained by, e.g., selfing NUN 09054 one or more times and/or cross-pollinating NUN 09054 with another lettuce plant of a different variety or breeding line, or with a lettuce plant of the invention one or more times. In particular, the invention provides for progeny that retain essentially all morphological and physiological characteristics of NUN 09054.

In still another embodiment, there is provided progeny of lettuce variety NUN 09054 produced by sexual or vegetative reproduction, grown from seeds, regenerated from the above-described plant parts, or regenerated from the above-described tissue culture of the lettuce variety or a progeny plant thereof, in which the sexually or vegetatively propagated plant has essentially all the morphological and physiological characteristics of lettuce variety NUN 09054.

Moreover, also an Essentially Derived Variety (EDV) of a lettuce plant designated NUN 09054 is provided. In one embodiment, an EDV exhibits one, two, three or more than three physiological and/or morphological characteristics which are different from those of NUN 09054 but which otherwise has essentially all physiological and morphological characteristics of a lettuce plant designated NUN 09054. In one embodiment, said EDV has essentially all physiological and/or morphological characteristics of a lettuce plant designated NUN 09054 but has one or two physiological and morphological characteristic(s) which is (are) different from those of the corresponding physiological and/or morphological characteristics of a plant designated NUN 09054 (i.e. has additional trait(s)).

In one embodiment, NUN 09054 may also be mutated (by e.g. irradiation, chemical mutagenesis, heat treatment, etc.) and mutated seeds or plants may be selected in order to change one or more characteristics of NUN 09054. Also natural mutants may be identified and used in breeding. Methods such as TILLING and/or EcoTILLING may be applied to lettuce populations in order to identify mutants. Similarly, NUN 09054 may be transformed and regenerated, whereby one or more chimeric genes are introduced into the variety. Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 09054, or progeny thereof, by transforming NUN 09054 or progeny thereof with a transgene that confers the desired trait, wherein the transformed plant retains essentially all the morphological and physiological characteristics of NUN 09054 or the progeny thereof and contains the desired trait.

The invention also provides for progeny of lettuce variety NUN 09054 obtained by further breeding with NUN 09054. In one aspect progeny are $F_1$ progeny obtained by crossing NUN 09054 with another plant or S1 progeny obtained by selfing NUN 09054. Also encompassed are F2 progeny obtained by selfing the $F_1$ plants. "Further breeding" encompasses traditional breeding (e.g., selfing, crossing, backcrossing), marker assisted breeding, and/or mutation breeding. In one embodiment, the progeny have all the physiological and morphological characteristics of variety NUN 09054 when grown under the same environmental conditions.

In one aspect haploid plants and/or double haploid plants of NUN 09054 are encompassed herein. Haploid and double haploid (DH) plants can for example be produced by anther or microspore culture and regeneration into a whole plant. For DH production chromosome doubling may be induced using known methods, such as colchicine treatment or the like.

The invention also provides a method of producing plants of variety designated NUN 09054, or its progeny, or an EDV, or a part thereof, comprising vegetative propagation of a plant designated NUN 09054. In one embodiment, said vegetative propagation comprises regenerating a whole plant from a part of variety designated NUN 09054. In one embodiment, said part of a plant is a cutting, root, stem, cell, protoplast, leaf meristem, bud, cell culture or a tissue culture (e.g., in vitro meristem culture, see Murakami and Oka, 1996, Plant Tissue Culture Letters 13 (3): 339). Thus, a vegetative propagated plant (or a part thereof) is provided having at least the essential morphological and physiological characteristics of a lettuce plant designated NUN 09054 when grown under the same environmental conditions. In some embodiments, said propagated plant has at least one or more morphological and physiological characteristic in common with a lettuce plant designated NUN 09054. Such characteristics are, e.g. the seed color, glossiness, shape of cotyledons etc. as outlined in this application.

The invention also provides for a method of producing a vegetatively propagated plant of variety designated NUN 09054, or a part thereof, comprising regeneration of said plant from a cell culture or a tissue culture. Also provided are plants which are regenerated from such a cell culture or tissue culture. In one embodiment such plants are haploid or double haploid plants of NUN 09054.

In still another aspect, the present invention provides a method of producing a plant derived from NUN 09054, the method comprising the steps of: (a) preparing a progeny plant derived from NUN 09054, wherein said preparing comprises crossing a plant of NUN 09054 either as a male or as a female parent with a second plant, or selfing NUN 09054, or vegetative propagation of NUN 09054, and (b) collecting seeds from said crossing or selfing or regenerating a whole plant from the vegetative cell- or tissue culture.

In one embodiment, crossing a plant of NUN 09054 either as a male or as a female parent with a second plant refers to cross-pollination of two plants of NUN 09054 or of crossing NUN 09054 with an EDV of NUN 09054, or crossing two EDVs of NUN 09054 with each other. In another embodiment, crossing a plant of NUN 09054 either as a male or as a female parent with a second plant refers to cross-pollination of NUN 09054 with a plant of another lettuce variety, breeding line or wild *Lactuca* species, e.g. *L. virosa* or *L. serriola*.

In yet a further aspect, the invention provides for a method of producing a new lettuce plant, e.g., a $F_1$ hybrid. The method comprises, crossing NUN 09054, either as male or as female parent, with a second lettuce plant which can be a second lettuce plant of the same variety, a lettuce plant of a different variety, a breeding line (e.g. an elite line) or a wild relative of lettuce (e.g., *Lactuca virosa* or *Lactuca serriola*) or genetic transformation techniques to produce a progeny of NUN 09054. The method may further comprise selfing the $F_1$ to produce an $F_2$ (and optionally further selfing selected $F_2$ plants to produce an $F_3$, etc.), and backcrossing an $F_1$, $F_2$, $F_3$, etc. to NUN 09054 or to an EDV of NUN 09054, to produce a backcross population ($BC_1$), which may then be selfed to produce a $BC_1S_1$ population, etc., or may be used to produce a $BC_2$ population, or other backcross populations.

Thus, in one aspect a method for developing a lettuce plant in a lettuce breeding program is provided, using a lettuce plant of the invention, or its parts, as a source of plant breeding material. Suitable plant breeding techniques are recurrent selection, backcrossing, pedigree breeding, line selection, mass selection, mutation breeding and/or genetic marker enhanced selection. For example, in one aspect, the method comprises crossing a lettuce plant designated NUN 09054, or progeny thereof, with a different lettuce plant selected from the group consisting of a plant of the same variety, a lettuce plant of a different variety, a (breeding) line, or a wild relative of lettuce (e.g., *L. virosa* or *L. serriola*), and wherein one or more offspring of the crossing are subject to one or more plant breeding techniques selected from the group consisting of recurrent selection, backcrossing, pedigree breeding, line selection, mass selection, mutation breeding and genetic marker enhanced selection (see e.g. Allard (1960), John Wiley & Sons, Inc,: Principles of plant breeding, Library of Congress Catalog Card Number: 60-14240).

In still yet another aspect; the present invention provides a method of producing a new plant comprising (a) crossing NUN 09054, or a progeny plant thereof, with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from NUN 09054. The plant derived from NUN 09054 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from NUN 09054 is obtained which possesses some of the desirable traits of the line as well as potentially other selected traits.

Pedrigee Selection

In one embodiment, Pedigree selection is used as breeding method for developing a lettuce variety. Pedigree selection, also known as the "Vilmorin system of selection," is described in, e.g., Allard, 1960, John Wiley & Sons, Inc.: Principles of plant breeding: 119-128, Library of Congress Catalog Card Number: 60-14240.

In general, selection is first practiced among $F_2$ plants. In the next season, the most desirable $F_3$ lines are first identified, then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

Thus, progeny in connection with Pedigree selection are either the generation (seeds) produced from the first cross ($F_1$) or selfing ($S_1$), or any further generation produced by crossing and/or selfing ($F_2$, $F_3$, $F_4$, $F_5$, $F_6$, $F_7$, etc.) and/or backcrossing ($BC_1$, $BC_2$, $BC_3$, $BC_4$, $BC_5$, $BC_6$, $BC_7$, etc.) one or more selected plants of the $F_1$ and/or $S_1$ and/or $BC_1$ generation (or plants of any further generation, e.g. the $F_2$) with another lettuce plant (and/or with a wild relative of lettuce). Using common breeding methods such as backcrossing or recurrent selection, one or more specific characteristics may be introduced into NUN 09054, to provide an EDV of NUN 09054.

In one embodiment, this invention is directed to methods for producing a lettuce plant by crossing a first parent lettuce plant with a second parent lettuce plant wherein either the first or second parent lettuce plant is lettuce NUN 09054. Further, both first and second parent lettuce plants can come from NUN 09054. Still further, this invention also is directed to methods for producing a NUN 09054-derived lettuce plant by crossing NUN 09054 with a second lettuce plant and growing the progeny seed, and repeating the crossing and growing steps with the NUN 09054-derived plant from zero to seven times. Thus, any such methods using NUN 09054 are part of this invention: selfing, backcrosses, hybrid production, crosses to populations, and the like. All plants produced using NUN 09054 as a parent are within the scope of this invention, including plants derived from NUN 09054. Advantageously, NUN 09054 is used in crosses with other, different, lettuce varieties to produce first generation (F1) lettuce hybrid seeds and plants with superior characteristics.

It should be understood that the lettuce can, through routine manipulation of cytoplasmic or other factors, be produced in a male-sterile form. Such embodiments are also contemplated within the scope of the present claims.

General crossing methods for lettuce are, e.g., described in US 2009/0271897 A1. Such methods include but are not limited to:

Manual removal of anther tubes from flowers, misting the designated male flowers to wash the pollen off prior to fertilization and pollen from another variety or donor parent is then introduced by gently rubbing the stigma and style of the donor parent to the maternal parent. Tags with the pertinent information on date and pedigree are then secured to the flowers in order to keep track. About 3 weeks after pollination, seeds are harvested when the involucres have matured. The seeds are eventually sown and in the presence of markers such as leaf color or leaf margins, the selfed or maternal seedlings or plants are identified. Generally, in case of crossing with a plant of a different variety, there are no visible markers and breeders must wait until the F2 generations when expected segregation patterns for the genetic character of interest can be followed.

Use of male sterility systems, such as genetic male sterility (GMS), see e.g. Hayashi et al. Euphytica Vol 180 (3): 429-436) or cytoplasmic male sterility (CMS). Genetically engineered sterility is also available. Non-limiting examples of genetically engineering male sterility in lettuce are by expression of a ribonuclease gene under the control of a tapetum-specific promoter (see Reynaerts et al., Scientia Horticulturae (1993) 55 (1-2): 125-129).

Other male sterile systems include the expression of beta-glucanase via a tapetum-specific promoter (see Curtis et al., Plant Science Limerick (1996) 113 (1): 113-119).

Also provided is a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce variety NUN 09054. Accordingly, a hybrid lettuce plant produced from crossing a first parent lettuce plant with a second parent lettuce plant and harvesting the resultant hybrid lettuce seed, wherein said first parent lettuce plant or said second parent lettuce plant is a lettuce plant designated NUN 09054 is provided, as well.

The invention provides for methods of producing EDVs (Essentially Derived Varieties), which retain essentially all morphological and physiological characteristics of NUN 09054 but which may differ from a lettuce plant designated NUN 09054 in one, two, three or more further morphological and/or physiological characteristics, but which are still genetically closely related to NUN 09054. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 09054 if its DNA fingerprint is at least 80%, 90%, 95%, 97% or 98% identical to the fingerprint of NUN 09054. In a preferred embodiment amplified fragment length polymorphism (AFLP) markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (van Eeuwijk and Law (2004), Euphytica 137: 129-137). In one embodiment a closely related plant of NUN 09050 has a Jaccard Similarity indez of higher than 0.96. See also the Guidelines on Essentially Derived Varieties for lettuce published by the ISF (http://www.worldseed.org/isf/edv.html), where the technical protocol for assessing the Jaccard index is outlined. The following 10 AFLP primer combinations can be used: E33/M59, E35/M48, E35/M49, E35/M59, E35/M60, E38/M54, E44/M48, E44/M49, E45/M48, E45/M49.

By crossing and/or selfing also (one or more) single traits may be introduced into NUN 09054 (e.g., using backcrossing breeding schemes), while retaining the remaining morphological and physiological characteristics of NUN 09054. For example, disease resistance genes may be introduced, genes responsible for one or more quality traits (such as head quality), yield, etc. Both single genes (dominant. semidominant or recessive) and one or more QTLs (quantitative trait loci) may be transferred into NUN 09054 by breeding with NUN 09054.

Any pest or disease resistance genes may be introduced into NUN 09054, progeny thereof or into an EDV of NUN 09054. Resistance against one or more of the following diseases is preferably introduced into plants of the invention: downy mildew, *Sclerotinia* rot, *Botrytis*, powdery mildew, anthracnose, bottom rot, corky root rot, lettuce mosaic virus, big vein, lettuce aphid, beet western yellows and aster yellows. Resistance against one or more of the following pests is preferably present or introduced into plants of the invention: *Sclerotinia minor* (leaf drop), *Sclerotinia sclerotiorum* (leaf drop), *Rhizoctonia solani* (bottom drop), *Erysiphe cichoracearum* (powdery mildew), *Fusarium oxysporum* f. sp. *lactucae* (*Fusarium* wilt) resistance. Other resistance genes, against pathogenic viruses (e.g. Lettuce infectious yellows virus (LIYV), lettuce mosaic virus (LMV), Cucumber mosaic virus (CMV), Beet western yellows virus (BWYV), Alfalfa mosaic virus (AMV)), fungi, bacteria or lettuce pests may also be introduced. In one embodiment resistance against *Nasonovia ribisnigri* biotype Nr:0 and/or Nr:1 is introduced into NUN 09054.

Transgene

Also provided is a method of producing a lettuce plant having a desired trait, wherein the method comprises transforming the lettuce plant of the invention with a transgene that confers the desired trait, wherein the transformed plant retains essential all phenotypic and morphological characteristics of a NUN 09054 plant of the invention and contains the desired trait. Thus, a transgenic lettuce plant is provided which is produced by the method described above, wherein the plant comprises the desired trait and essentially all of the physiological and morphological characteristics of a NUN 09054 plant.

Many useful traits that can be introduced into NUN 09054 by e.g. crossing NUN 09054 with a transgenic lettuce plant comprising a desired transgene, as well as by directly introducing a transgene into NUN 09054 (or an EDV, or progeny of NUN 09054) by genetic transformation techniques. Genetic transformation may, therefore, be used to insert a selected transgene into the lettuce plants of the invention or may, alternatively, be used for the preparation of transgenic lettuce plants which can then be used as a source of the transgene(s), which can be introduced into NUN 09054 by e.g. backcrossing. Methods for the transformation of plants, including lettuce, are well known to those of skill in the art.

DNA sequences, whether from a different species or from the same species, which are inserted into the genome using transformation, are referred to herein collectively as "transgenes". A "transgene" also encompasses antisense, or sense and antisense sequences capable of gene silencing. Thus, the present invention also relates to transgenic NUN 09054 plants. In some embodiments of the invention, a transgenic NUN 09054 plants may contain at least one transgene but could contain at least 1, 2, 3, 4, 5, 6, or more transgenes.

One embodiment of the invention is a process for producing progeny of a plant designated NUN 09054 further comprising a desired trait, said process comprising transforming a NUN 09054 plant (or a cell or tissue of NUN 09054) with at least one transgene that confers a desired trait and/or crossing a plant designated NUN 09054 with a transgenic lettuce plant comprising a desired transgene so that the genetic material of the progeny that results from the cross contains the transgene(s). The DNA of the transgene is operatively linked to a regulatory element active in plant cells (especially a promoter) and the transgene confers a trait selected from the group consisting of male sterility, male fertility, herbicide resistance, insect resistance, disease resistance, improved yield, improved nutritional quality or improved biotic or abiotic (e.g. drought or salt) stress tolerance. Another embodiment is the product produced by this process. In one embodiment the desired trait which is based on a transgene may be one or more of herbicide resistance, insect resistance, disease resistance, stress tolerance, modified fatty acid or modified carbohydrate metabolism. The specific transgene may be any known in the art or listed herein, including, a polynucleotide sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to nematodes, downy mildew, *Sclerotinia* rot, *Botrytis*, powdery mildew, anthracnose, bottom rot, corky root rot, lettuce mosaic virus, big vein, lettuce aphid, beet western yellows and aster yellows, *Sclerotinia minor* (leaf drop), *Sclerotinia sclerotiorum* (leaf drop), *Rhizoctonia solani* (bottom drop), *Erysiphe cichoracearum* (powdery mildew), *Fusarium oxysporum* f. sp. *Lactucae* (*fusarium* wilt), lettuce infectious yellows virus (LIYV), lettuce mosaic virus (LMV), Cucumber mosaic virus (CMV), Beet western yellows virus (BWYV), and Alfalfa mosaic virus (AMV).

Numerous methods for plant transformation have been developed, including biological and physical plant transformation protocols (see, e.g., Glick, B. R. and Thompson, J. E. Eds. (CRC Press, Inc., Boca Raton (1993): 67-88 and Armstrong, "The First Decade of Maize Transformation: A Review and Future Perspective" Maydica 1999 (44):101-109). In addition, expression vectors and in vitro culture methods for plant cell or tissue transformation and regeneration of plants are available. See, e.g., Glick, B. R. and Thompson, J. E. Eds. (CRC Press, Inc., Boca Raton (1993): 89-119).

A genetic trait which has been engineered into the genome of a particular lettuce plant may then be moved into the genome of another lettuce plant (e.g. another variety) using traditional breeding techniques that are well known in the plant breeding arts. For example, a backcrossing approach is commonly used to move a transgene from a transformed lettuce variety into an already developed lettuce variety, and the resulting backcross conversion plant will then comprise the transgene(s).

Various genetic elements can be introduced into the plant genome using transformation. These elements include, but are not limited to genes, coding sequences, inducible-, constitutive-, and tissue specific promoters, enhancing sequences, and signal and targeting sequences. For example, see the traits, genes, and transformation methods listed in U.S. Pat. No. 6,118,055.

Plant transformation involves the construction of an expression vector which will function in plant cells. Such a vector comprises DNA comprising a gene under control of, or operatively linked to, a regulatory element (for example a promoter). The expression vector may contain one or more such operably linked gene/regulatory element combinations. The vector(s) may be in the form of a plasmid and can be used alone or in combination with other plasmids to provide transformed lettuce plants using transformation methods as described below to incorporate transgenes into the genetic material of the lettuce plant(s).

Although also marker-free transformation methods are known, expression vectors generally include at least one genetic marker operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Thus, vectors used for the transformation of lettuce cells are not limited so long as the vector can express an inserted DNA in the cells. For example, vectors comprising promoters for constitutive gene expression in lettuce cells (e.g., cauliflower mosaic virus 35S promoter) and promoters inducible by exogenous stimuli can be used. Examples of suitable vectors include pBI binary vector. The "lettuce cell" into which the vector is to be introduced includes various forms of lettuce cells, such as for example cultured cell suspensions, protoplasts, leaf sections, and callus.

Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin (see, e.g., Fraley et al., Proc. Natl. Acad. Sci. USA (1983), 80: 4803-4807). Another commonly used selectable marker gene is the hygromycin phosphotransferase gene which confers resistance to the antibiotic hygromycin (see, e.g., Vanden Elzen et al., Plant Mol. Biol, (1985) 5: 299-302).

Additional selectable marker genes of bacterial origin that confer resistance to antibiotics include gentamycin acetyl transferase, streptomycin phosphotransferase and aminoglycoside-3'-adenyl transferase, the bleomycin resistance determinant. Other selectable marker genes confer resistance to herbicides such as glyphosate, glufosinate or bromoxynil. Further selectable markers such as mouse dihydrofolate reductase and plant acetolactate synthase are well known in the art. Also known are marker genes for plant transformation which require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. The use of such markers is also encompassed by the present invention.

The gene encoding Green Fluorescent Protein (GFP) can also be utilized as a marker for gene expression in prokaryotic and eukaryotic cells (Chalfie et al., Science (1994) 263: 802-805). GFP and mutants of GFP may be used as screenable markers.

Genes included in expression vectors must be driven by a nucleotide sequence comprising a regulatory element, for example, a promoter. Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary promoters are well known in the art such as inducible promotors, constitutive promoters, tissue-specific promotors or tissue-preferred promoters. One example is the cauliflower mosaic virus 35S promoter.

Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized.

The presence of a signal sequence directs a polypeptide to either an intracellular organelle (e.g. chloroplasts) or subcellular compartment or for secretion to the apoplast. Many signal sequences are known in the art (see, e.g., Becker et al., Plant Mol. Biol. (1992) 20: 49-60; or Knox, C., et al., Plant Mol. Biol. (1987) 9: 3-17).

By means of the present invention, plants can be genetically engineered to express various phenotypes of horticultural interest. Through the transformation of lettuce the expression of genes can be altered to enhance disease resistance, insect resistance, herbicide resistance, stress tolerance, horticultural quality, and other traits. Transformation can also be used to insert DNA sequences which control or help control male sterility or fertility restoration. DNA sequences native to lettuce as well as non-native DNA sequences can be transformed into lettuce and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including, but not limited to, knock-outs (such as by insertion of a transposable element such as mu) or other genetic elements such as a FRT, Lox or other site specific integration site, antisense technology, co-suppression, RNA interference, virus-induced gene silencing, target-RNA-specific ribozymes, ribozymes, oligonucleotide mediated targeted modification, Zinc-finger targeted molecules; and other methods or combinations of the above methods known to those of skill in the art.

Likewise, by means of the present invention, other genes can be expressed in transformed plants. More particularly, plants can be genetically engineered to express various phenotypes of interest.

Exemplary nucleic acids which may be introduced to the lettuce lines of this invention include, for example, DNA sequences or genes from another species, or even genes or sequences which originate from, or are present in, the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Non-limiting examples of particular genes and corresponding phenotypes one may choose to introduce into a lettuce plant include one or more genes for insect tolerance, such as a *Bacillus thuringiensis* (B.t.) gene, disease tolerance such as genes for fungal or bacterial disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). A more detailed list of genes implicated in this regard includes, but is not limited to, genes that confer resistance to pests or disease and that encode: a) plant disease resistance genes (plant defenses are often activated by specific interaction between the product of a disease resistance gene (R) in the plant and the product of a corresponding avirulence (Avr) gene in the pathogen, b) genes conferring resistance to a pest, such as a nematode or insects (e.g., insect-specific hormones or pheromones, or insect-specific peptides or neuropeptides which, upon expression, disrupts the physiology of the affected pest), c) an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic, d) a viral-invasive protein or a complex toxin derived therefrom, e.g., the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, and tobacco mosaic virus), e) a virus-specific antibody, f) a developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase, g) genes involved in the Systemic Acquired Resistance (SAR) Response and/or the pathogenesis-related genes or antifungal genes, h) cystatin and cysteine proteinase inhibitors, i) defensin genes, j) genes conferring virus resistance, e.g. coat protein genes conferring resistance against Lettuce big vein disease.

Also included, but not limited to, are genes that confer resistance to an herbicide, e.g.: a) a herbicide that inhibits the growing point or meristem, such as an imidazolinone or a sulfonylurea. Exemplary genes in this category code for mutant ALS and AHAS enzyme, b) Glyphosate (resistance, e.g., conferred by mutant 5-enolpyruvylshikimate-3-phosphate synthase (EPSPS) and aroA genes, respectively, and other phosphono compounds such as glufosinate, and pyridinoxy or phenoxy proprionic acids and cyclohexanediones, c) a nucleotide sequences of glutamine synthetase genes which confer resistance to herbicides such as L-phosphinothricin, d) Nucleotide sequence of a PAT gene, e) a herbicide that inhibits hydroxyphenylpyruvate dioxygenase, f) a herbicide that inhibits photosynthesis, g) protoporphyrinogen oxidase (protox) enzyme serves as the target for a variety of herbicidal compounds.

Also included, but not limited to, are genes that confer or contribute to a value-added trait, such as: a) modified fatty acid metabolism, b) decreased phytate, c) modified carbohydrate composition, d) altered antioxidant content or composition, Also included, but not limited to, are genes that control male sterility.

Also included, but not limited to, are genes that create a site for site specific DNA integration, genes that affect abiotic stress resistance, and other genes and transcription factors that affect plant growth and other traits such as yield, flowering, plant growth, and/or plant structure, can be introduced or introgressed into plants.

Transgenic lettuce can also be used as protein-factory, e.g. for the production of edible vaccines.

A vector can be introduced into lettuce cells by known methods, such as the polyethylene glycol method, polycation method, electroporation, *Agrobacterium*-mediated transfer, microprojectile bombardment and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner. An example of electroporation of lettuce protoplasts is presented in Chupeau et al. (1989; Bio/Technology 7: 503-508).

Microprojectile bombardment techniques are widely applicable, and may be used to transform virtually any plant species. Examples involving microprojectile bombardment transformation with lettuce can be found in, e.g., Elliott et al. Phys. Rev. Lett. (2004) 92: 095501.

When using microprojectile bombardment, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target lettuce cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

*Agrobacterium*-mediated transfer is another widely applicable system for introducing transgenes into plant cells. Modern *Agrobacterium* transformation vectors are capable of replication in *E. coli* as well known in the art. For example, U.S. Pat. No. 5,349,124 describes a method of transforming lettuce plant cells using *Agrobacterium*-mediated transformation. By inserting a chimeric gene having a DNA coding sequence encoding for the full-length B.t. toxin protein that expresses a protein toxic toward Lepidopteran larvae, this methodology resulted in lettuce having resistance against such insects.

Transformation of plant protoplasts also can be achieved using methods based on calcium phosphate precipitation, polyethylene glycol treatment, electroporation, and combinations of these treatments (see, e.g., Neuhaus and Spangenberg, Physiologia Plantarum (1990) 79 (1): 213-217).

The foregoing methods for transformation would typically be used for producing a transgenic plant. The transgenic plant could then be crossed with another (non-transgenic or transgenic) plant in order to produce a new transgenic plant. Alternatively, a genetic trait that has been engineered into a particular lettuce plant using the foregoing transformation techniques could be moved into another plant using traditional breeding techniques that are well known in the plant breeding arts.

Products and Package

Also provided are plant parts derived from variety NUN 09054, or from a vegetatively propagated plant of NUN 09054, being selected from the group consisting of: harvested (mature or immature) leaves or parts thereof, pollen, ovules, cells, heads, cotyledons, seeds or parts thereof, stalks or parts thereof, roots or parts thereof, cuttings, or parts thereof, flowers, florets, or flower buds.

In one embodiment, the invention provides for extracts of a plant described herein and compositions comprising or consisting of such extracts. In a preferred embodiment, the extract consists of or comprises tissue of a plant described herein or is obtained from such tissue. For example sesquiterpene-lactones such as lactucin, lactucid or lactucopicrin; or triterpenes such as amyrin, lactucerol or taraxasterol cyanine may be an extract obtained from leaf tissue and used to make a health-beneficial composition (e.g., a pharmaceutical or nutraceutical composition).

The invention also provides for a food or feed product comprising or consisting of a plant part described herein and/or an extract from a plant part described herein. The food or feed product may be fresh or processed, e.g., canned, steamed, boiled, fried, blanched and/or frozen etc.

A lettuce plant designated NUN 09054, a progeny thereof, a derived variety thereof (such as EDV), and parts of the afore-mentioned plants/varieties can be suitably packed for, e.g., transport, and/or sold fresh. Such parts encompass any cells, tissues and organs obtainable from the seedlings or plants, such as but not limited to: heads, cuttings, pollen, leaves, parts of leaves, and the like. Heads and leaves may be harvested immature, as baby-leaf, or mature. A plant, plants or parts thereof may be packed in a container (e.g., bags, cartons, cans, etc.) alone or together with other plants or materials. Parts can be stored and/or processed further.

Encompassed are therefore also food or feed products comprising one or more of such parts, such leaves or parts thereof obtainable from NUN 09054 plant, a progeny thereof a derived variety thereof (such as EDV), and parts of the afore-mentioned plants/varieties.

For example, containers such as cans, boxes, crates, bags, cartons, Modified Atmosphere Packagings, films (e.g. biodegradable films), etc. comprising plant parts of plants (fresh and/or processed) designated NUN 09054 are also provided herein.

Color

The "red color" of a plant in accordance with the present invention can be determined by comparing the color of, e.g., fourth or mature leaves with fourth or mature leaves of another plant such as a OBREGON plant grown under the same conditions. The skilled person can, e.g., use a RHS colour chart: 2007 as described herein.

Moreover, the concentration of anthocyanins can be determined by using standard methods known in the art. One of these methods is, e.g., described in US 2009/0106867. For example, a headed and mature lettuce plant is harvested and outer leaves are taken off. In general the four oldest leaves can be regarded as outer leaves. The skilled person is aware that the oldest leaves of a lettuce plant are located at the outer part of the lettuce plant.

The leaves can be pulverized and analysed for anthocyanins. Pulverization can be achieved by, e.g., freezing the leaves and grinding them with a sledgehammer and further grinding the crude powder with a knife mill such as a Grindomix GM 200 (Retsch, 5" 3000 rpm followed by 5" 5000 rpm) using the free floating lid in presence of liquid nitrogen to achieve a powder for analysis of anthocyanins.

As an example for the analysis, said powder is added to a solution of HCl in methanol (e.g. 1 M HCl in 50% methanol). The amount of sample depends from the color. Generally 2-40 ml/g sample is used. The used volume (ml) is noted. A part of the solution is freed from insoluble parts, e.g., by using a centrifuge at 4° C., 13000 rpm for around 4 min.

The spectrum of 360-900 nm is measured and the absorbance at 523 nm (if necessary after dilution with extraction liquid) and the maximum wavelength ($\lambda_{max}$) are determined. $\lambda_{max}$ should be close to 523 nm.

Moreover, chlorophylls are measured by immediately adding 100% methanol to the test sample of the anthocyanin analysis. The volume (ml) used is noted.

The spectrum of 360-900 nm is measured and the absorbance at 665 nm (if necessary after dilution with extraction liquid) and the maximum wavelength ($\lambda_{max}$) determined. $\lambda_{max}$ should be close to 665 nm.

The A523 and A665 are corrected to represent the absorbance of a solution of 1 g fresh weight in 10 ml extraction volume. The corrected A523 and A665 are calculated with a correction for weighted sample (in g), extraction volume (in ml) and if necessary dilution using the following formula:

$$A_{corrected.} = \frac{A_{measured} * extr. \ volume}{weight * 10} * dilution$$

The ratio A523/A665 is calculated.

Deposit Information

A total of 2500 seeds of the variety NUN 09054 (also called "MULTIRED 54") were deposited by Nunhems B.V. on Jan. 14, 2014, at the NCIMB Ltd., Ferguson Building, Craibstone Estate, Bucksburn, Aberdeen AB21 9YA, United Kingdom (NCIMB). The deposit has been assigned Accession Number NCIMB 42205. A deposit of NUN 09054 and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Various modifications and variations of the described products and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in plant breeding, chemistry, biology or related fields are intended to be within the scope of the following claims.

EXAMPLES

Development of NUN 09054

The variety NUN 09054 was developed from an initial cross between a lettuce variety and a breeding line. The female and male parents were crossed to produce hybrid ($F_1$) seeds. After the cross, F1 plants were self pollinated. From the second to the fifth generation pedigree selection was performed. From the sixth to the ninth generation line selection was performed.

Variety NUN 09054 has been observed for at least three generations in different trials on different locations and during seed increase and is uniform and stable.

The variety is, therefore, uniform and genetically stable. This has been established through evaluation of horticultural characteristics. Independent seed production events resulted in no observable deviation in genetic stability.

The seeds of NUN 09054 can be grown to produce plants and parts thereof (e.g. heads or leaves). The variety NUN 09054 can be propagated by seeds or vegetative propagation.

MULTIRED 54 characteristics were compared with those of OBREGON and GRAND RAPIDS according to standards of the U.S. Department of Agriculture, Agricultural Marketing Service, Science and Technology, Plant Variety Protection Office, Beltsville, Md. 20705. Trials were carried out by Nunhems USA Inc., e.g., in Acampo, Calif. (US) in 2012 (Sow date: Jan. 31, 2012), Salinas (Mar. 9, 2011, duration 50 days), King City (Sow date: Apr. 13, 2011, duration 45 days), Hollister (Sow date: Jul. 26, 2011, duration 45 days) and Yuma, Ariz. (US) (Sow date: Nov. 15, 2011, duration 55 days).

Characteristics of NUN 09054

Table 1 shows the USDA descriptors of NUN 09054 (MULTIRED 54; this application), OBREGON and GRAND RAPIDS of a field trial in Acampo, Calif., US. 20 plants or plant parts were randomly selected from two replications of 100 plants each of a field trial in Acampo. These 20 plants were used to measure characteristics. The values are mean values. Some of the most significant differences are highlighted in bold.

TABLE 1

| USDA number | USDA descriptor | NUN 09054 | OBREGON | GRAND RAPIDS |
|---|---|---|---|---|
| 1 | Plant type<br>1 = Cutting/Leaf | 1 | 1 | 1 |
| 2 | Seed | | | |
| | Color<br>1 = white, 2 = black, 3 = brown | 2 | 1 | 2 |
| 3 | Cotyledon to fourth leaf stage | | | |
| | Shape of Cotyledons<br>1 = broad, 2 = intermediate, 3 = spatulate | 2 | 2 | 2 |
| | Shape of fourth leaf<br>3 = oval, 6 = pinnately lobed | 6 | 6 | 3 |
| | Apical margin<br>1 = entire, 2 = crenate/gnawed, 3 = finely dentate, 4 = moderately dentate, 5 = coarsely dentate, 6 = incised, 7 = lobed, 8 = other (undulate) | 6 | 6 | 8 |
| | Basal margin<br>1 = entire, 2 = crenate/gnawed, 3 = finely dentate, 4 = moderately dentate, 5 = coarsely dentate, 6 = incised, 7 = lobed, 8 = other (undulate) | 6 | 5 | 5 |
| | Undulation<br>1 = flat, 2 = slight, 3 = medium, 4 = marked | 4 | 4 | 3 |
| | Green color<br>1 = yellow green, 2 = light green, 3 = medium green, 4 = dark green | 2 | 3 | 2 |
| | Anthocyanin: | | | |
| | Distribution<br>1 = absent, 2 = margin only, 3 = spotted, 4 = throughout | 4 | 2 | 1 |
| | Concentration<br>1 = light, 2 = moderate, 3 = intense | 3 | 2 | — |
| | Reflexing<br>2 = apical margin, 3 = lateral margins | 1 | 1 | 2 |
| 4 | Mature leaves (harvest mature outer leaves): | | | |
| | Margin: | | | |
| | Incision depth<br>1 = absent/shallow (Dark Green Boston), 2 = moderate (Vanguard), 3 = deep (Great Lakes 659) | 3 | 2 | 2 |
| | Indentation<br>1 = entire, 2 = shallowly dentate (Great Lake 65), 3 = deeply dentate (Great Lake 659) | 3 | 3 | 2 |
| | Undulations of the apical margin<br>1 = absent/slight (Dark Green Boston), 2 = moderate (Vanguard), 3 = strong (Great Lakes 659) | 3 | 3 | 3 |
| | Green color<br>1 = very light green, 2 = light green, 3 = medium green, 4 = dark green, 6 = other | 4 | 2 | 1 |
| | Anthocyanin: | | | |
| | Distribution<br>1 = absent, 3 = spotted (California Cream Butter), 4 = throughout (Prize Head) | 4 | 2 | 1 |
| | Concentration<br>1 = light, 2 = moderate, 3 = intense | 3 | 2 | 1 |
| | Size<br>1 = small, 2 = medium, 3 = large | 1 | 2 | 3 |
| | Glossiness<br>1 = dull, 2 = moderate, 3 = glossy | 3 | 1 | 2 |
| | Blistering<br>1 = absent/slight, 2 = moderate, 3 = strong | 1 | 1 | 3 |
| | Leaf thickness<br>1 = thin, 2 = intermediate, 3 = thick | 2 | 2 | 2 |
| | Trichomes<br>1 = absent, 2 = present | 1 | 1 | 1 |
| 5 | Plant | | | |
| | Spread of frame leaves | 15.5 cm | 19.1 cm | 18.7 cm |
| | Head diameter (market trimmed with single cap leaf) | — cm | — cm | — cm |
| | Head shape<br>1 = flattened, 2 = slightly flattened, 4 = elongate, 5 = non-heading | 5 | 5 | 5 |
| | Head size class<br>1 = small, 2 = medium, 3 = large | 1 | 2 | 3 |

TABLE 1-continued

| USDA number | USDA descriptor | NUN 09054 | OBREGON | GRAND RAPIDS |
|---|---|---|---|---|
| | Head per carton | — | — | — |
| | Head weight | — g | — g | — g |
| | Head firmness<br>1 = loose, 3 = Firm, 4 = very firm | 1 | 1 | 1 |
| 6 | Butt | | | |
| | Shape<br>1 = slightly concave, 2 = flat, 3 = rounded | 3 | 3 | 3 |
| | Midrib<br>1 = flattened; 2 = moderately raised; 3 = prominently raised | 1 | 1 | 1 |
| 7 | Core | | | |
| | Diameter at base of head | 5.5 mm | 7.6 mm | 7.3 mm |
| | Core height from base of head to apex | 5.3 mm | 7.0 mm | 7.2 mm |
| 8 | Bolting (first water date: Oct. 3, 2011) | | | |
| | Number of days from first water date to seed stalk emergence (note: First water date is the date seed first receives adequate moisture to germinate. This often equals planting date). | — | — | — |
| | Bolting class<br>1 = very low, 3 = medium, 4 = rapid, 5 = very rapid | — | — | — |
| | Height of mature seed stalk | — cm | — cm | — |
| | Spread of bolter plant (at widest point) | — cm | — cm | — |
| | Bolter Leaves | — | — | — |
| | 1 = straight; 2 = curved | | | |
| | Margin | — | — | |
| | 1 = entire; 2 = dentate | | | |
| | Color | — | — | — |
| | 1 = light green, 2 = medium green | | | |
| 9 | Maturity (earliness of harvest-mature head formation) | 50 days (spring)<br>45 days (summer)<br>45 days (fall)<br>55 days (winter) | 50 days (spring)<br>45 days (summer)<br>45 days (fall)<br>55 days (winter) | 47 days (spring)<br>45 days (summer)<br>45 days (fall)<br>55 days (winter) |
| 10 | Adaptation: | — | — | — |
| | Primary regions of adaptation: | Southwest (CA and/or AZ desert, West Coast | | |
| | Season<br>0 = not tested, 1 = not adapted, 2 = adapted | Fall (2), Winter (2), Spring (2), Summer (2) | | — |
| | Greenhouse<br>0 = not tested, 1 = not adapted, 2 = adapted | 1 | — | — |
| | Soil type<br>1 = mineral, 2 = organic, 3 = both | 3 | — | — |
| | Insects | | | |
| | Lettuce Aphids<br>1 = immune; 3 = resistant; 5 = moderately resistant; 7 = susceptible; 9 = highly sisceptible | 3 | 7 | — |

— = not measured

These are typical values. Values may vary due to environment. Other values that are substantially equivalent are also within the scope of the invention.

Figure 1:
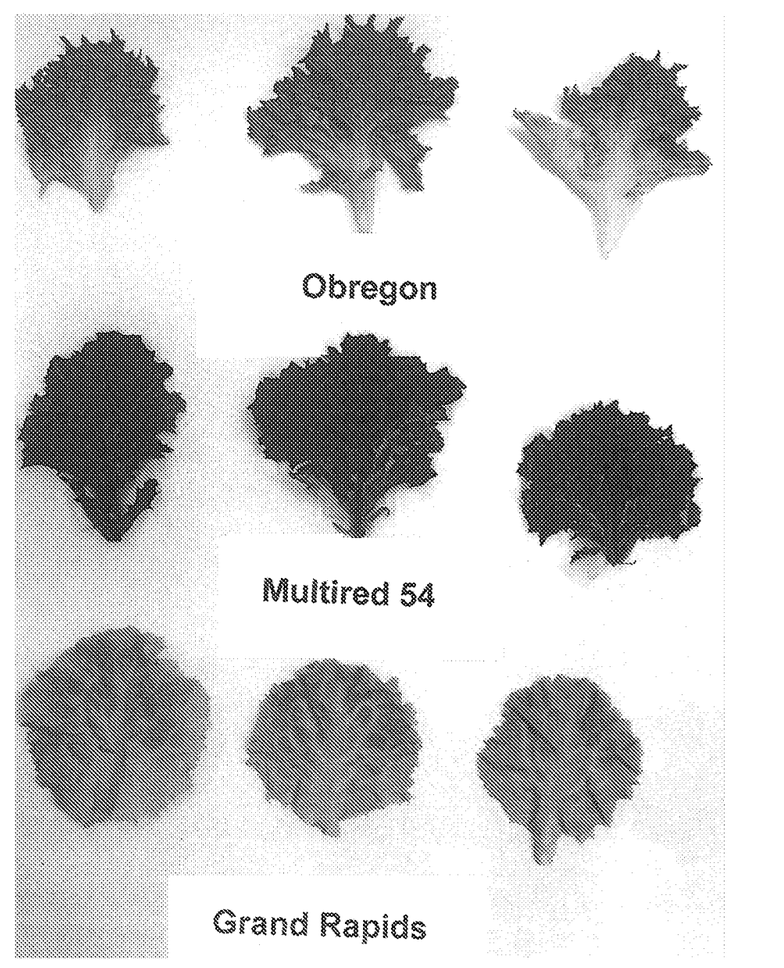
FIG. 1, shows the differences in shading and shape of a typical fourth leaves of NUN 09054, OBREGON and GRAND RAPIDS.

Without limiting the scope of the present invention, picture 1 shows the different shape of mature leaves of NUN 09054 and mature leaves of OBREGON. The pictures may also be available as colored pictures on request.

The invention claimed is:

1. A lettuce plant, designated NUN 09054, or part thereof, a representative sample of seeds of which having been deposited under Accession Number NCIMB 42205.

2. A seed designated NUN 09054, a representative sample of seeds having been deposited under Accession Number NCIMB 42205.

3. A plant, or a part thereof, produced by growing the seed of claim 2.

4. A part of the plant of claim 1, wherein the part is a head or a leaf or a part thereof.

5. A cell culture or tissue culture of the lettuce plant of claim 1.

6. A lettuce plant which is regenerated from the part of the plant of claim 1 and comprises essentially all physiological and morphological characteristics of NUN 09054.

7. A lettuce plant which is regenerated from the cell culture or tissue culture of claim 5 and comprises essentially all physiological and morphological characteristics of NUN 09054.

8. A progeny plant of lettuce variety designated NUN 09054 obtained by further breeding with said variety, wherein said progeny plant has essentially all physiological and morphological characteristics of the variety designated NUN 09054 when grown under the same environmental conditions, and wherein representative seed of lettuce variety NUN 09054 has been deposited under Accession Number NCIMB 42205.

9. An Essentially Derived Variety of NUN 09054 having one, two or three physiological and/or morphological characteristics which are different from those of NUN 09054 and which otherwise has essentially all physiological and morphological characteristics of the lettuce plant designated NUN 09054, wherein representative seed of lettuce variety NUN 09054 has been deposited under Accession Number NCIMB 42205.

10. An Essentially Derived Variety of NUN 09054 according to claim 9 having one or two physiological and/or morphological characteristics which are different from those of NUN 09054 and which otherwise has essentially all physiological and morphological characteristics of a lettuce plant designated NUN 09054 obtainable by selecting a natural or induced mutant, or a somaclonal variant from a population of plants designated NUN 09054.

11. A package comprising a head, leaves or parts thereof of a plant of claim 1.

12. A package comprising the seed of claim 2.

13. A seed pellet comprising the seed of claim 2.

14. A method of producing a lettuce plant, comprising crossing the plant of claim 1 with a second lettuce plant one or more times and/or selfing the plant of claim 1 one or more times, and selecting progeny from said crossing and/or selfing.

15. A method of producing a lettuce plant derived from NUN 09054 comprising the steps of:
 (a) preparing a progeny plant derived from NUN 09054 by crossing the plant of claim 1 with itself or with a second lettuce plant;
 (b) crossing the progeny plant with itself or a second lettuce plant to produce a seed of a progeny plant of a subsequent generation;
 (c) growing a progeny plant of a subsequent generation from said seed and crossing the progeny plant of a subsequent generation with itself or a second lettuce plant; and
 (d) repeating step b) and/or c) for at least 1 more generation to produce a lettuce plant derived from NUN 09054.

16. A method of producing a hybrid lettuce seed, comprising crossing a first parent lettuce plant with a second parent lettuce plant and harvesting the resultant hybrid lettuce seed, wherein said first parent lettuce plant or said second parent lettuce plant is a lettuce plant of claim 1.

17. A hybrid lettuce seed produced by crossing a first parent lettuce plant with a second parent lettuce plant and harvesting the resultant hybrid lettuce seed, wherein said first parent lettuce plant or said second parent lettuce plant is a lettuce plant of claim 1.

18. A method of introducing a single locus conversion into a lettuce plant designated NUN 09054 comprising:
 (a) crossing a plant designated NUN 09054 with a second plant comprising a desired single locus to produce a F1 progeny plant, wherein representative seed of NUN 09054 has been deposited under Accession Number NCIMB 42205;
 (b) optionally selfing said F1 progeny plant to produce a F2 progeny plant having said single locus;
 (c) crossing said F1 or F2 progeny plant of step (a) or step (b), respectively, with a plant of NUN 09054, to produce backcross progeny plants;
 (d) selecting backcross progeny plants that have the single locus and otherwise essentially all physiological and morphological characteristics of a plant designated NUN 09054; and
 (e) repeating steps (c) and (d) one or more times in succession to produce selected second or higher backcross progeny plants that comprise the single locus and otherwise comprise essentially all physiological and morphological characteristics of a plant designated NUN 09054.

19. The method of claim 18, wherein the single locus confers a trait, wherein the trait is pest resistance or disease resistance.

20. The method of claim 19, wherein the single locus confers at least one trait, wherein said trait is at least one trait selected from the group consisting of resistance against Nasonovia ribisnigri Nr: 1 or Nr: 0, downy mildew, Sclerotinia rot, Botrytis, powdery mildew, anthracnose, bottom rot, corky root rot, lettuce mosaic virus, big vein, lettuce aphid, beet western yellows and aster yellows, Sclerotinia minor (leaf drop), Sclerotinia sclerotiorum (leaf drop), Rhizoctonia solani (bottom drop), Erysiphe cichoracearum (powdery mildew), Fusarium oxysporum f. sp. Lactucae (fusarium wilt), lettuce infectious yellows virus (LIYV), lettuce mosaic virus (LMV), Cucumber mosaic virus (CMV), Beet western yellows virus (BWYV), Alfalfa mosaic virus (AMV), nematodes and herbicides.

21. A plant of claim 1 wherein said plant has at least the essential physiological and morphological characteristics of the variety designated NUN 09054 and further comprises at least one transgene that confers a desired trait.

\* \* \* \* \*